US011896613B2

(12) United States Patent
Nakagawa et al.

(10) Patent No.: US 11,896,613 B2
(45) Date of Patent: Feb. 13, 2024

(54) FUNCTIONAL FOOD

(71) Applicant: COOPERATIVE ASSOCIATION LATEST, Wakayama (JP)

(72) Inventors: Kazuki Nakagawa, Wakayama (JP); Daisuke Kawakami, Wakayama (JP); Hirotoshi Utsunomiya, Wakayama (JP); Ryohei Kono, Wakayama (JP); Yoshiharu Okuno, Wakayama (JP)

(73) Assignee: COOPERATIVE ASSOCIATION LATEST, Wakayama (JP)

( * ) Notice: Subject to any disclaimer, the term of this patent is extended or adjusted under 35 U.S.C. 154(b) by 576 days.

(21) Appl. No.: 17/109,858

(22) Filed: Dec. 2, 2020

(65) Prior Publication Data

US 2021/0085712 A1  Mar. 25, 2021

Related U.S. Application Data

(63) Continuation of application No. PCT/JP2019/017654, filed on Apr. 25, 2019.

(30) Foreign Application Priority Data

Jun. 7, 2018  (JP) ................. 2018-109371

(51) Int. Cl.
*A61K 33/44* (2006.01)
*A23L 33/00* (2016.01)
*A23L 29/00* (2016.01)
*A61P 3/04* (2006.01)
*A61K 9/14* (2006.01)

(52) U.S. Cl.
CPC ............ *A61K 33/44* (2013.01); *A23L 29/015* (2016.08); *A23L 33/30* (2016.08); *A61K 9/14* (2013.01); *A61P 3/04* (2018.01)

(58) Field of Classification Search
CPC ....... A61L 33/44; A61L 29/015; A61K 33/30; A61K 9/14; A61P 3/04
See application file for complete search history.

(56) References Cited

U.S. PATENT DOCUMENTS

2013/0171206 A1* 7/2013 Sonobe .................... A61K 9/16
424/125

FOREIGN PATENT DOCUMENTS

| JP | H1129485 A | 2/1999 |
|---|---|---|
| JP | 2001322808 A | 11/2001 |
| JP | 2003000147 A * | 1/2003 |
| JP | 2005305406 A | 11/2005 |
| JP | 2007261918 A | 10/2007 |
| JP | 2012136484 A | 7/2012 |
| KR | 20140136829 A * | 12/2014 |
| WO | 2004039381 A1 | 5/2004 |
| WO | 2016031908 A1 | 3/2016 |

OTHER PUBLICATIONS

Bincho charcoal powder, bamboo charcoal powder (industrial material), collaborative linking LATTEST, Feb. 11, 2017, Retrieved from the Internet: https://web.archive.org/web/20170211102223/http://www.latest.or.jp/36.htm. With machine translation.
International Searching Authority. International Search Report and Written Opinion for application PCT/JP2019/017654, dated Jun. 11, 2019. With machine translation.
Japan Ministry of Health, Labour and Welfare. Medicinal Carbon. The Japanese Pharmacopoeia. JP XVII. 2016. pp. 1200-1201.
Japan Hospital Pharmacy Association. Medicinal Carbon. Medical Product Interface Form. Jan. 2013. With translation.

* cited by examiner

*Primary Examiner* — Shirley V Gembeh
(74) *Attorney, Agent, or Firm* — Quarles & Brady LLP; Yakov S. Sidorin

(57) ABSTRACT

The present invention provides a functional food that utilizes health-promoting effects of charcoal, is readily ingested, has no adverse side effect, and has an effect of improving and repressing obesity. The functional food includes a charcoal composition having at least one of a bamboo charcoal, a Bincho charcoal, an activated bamboo charcoal and an activated Bincho charcoal, and both of the activated bamboo charcoal and the activated Bincho charcoal have a bulk density of 0.3 to 0.6 g/ml, an average particle size of 10 μm or smaller, a BET specific surface area of 1000 to 1200 $m^2/g$, and an iodine adsorption amount of 1000 to 1300 mg/g.

14 Claims, 5 Drawing Sheets

100μm

200μm

———— 100μm

———— 100μm

———— 100μm

——— 1 μm

FIG. 4 Effects of bamboo charcoal and Bincho charcoal on weight gain

FIG. 2 GC-MS chromatogram and indole MS fragment in control group

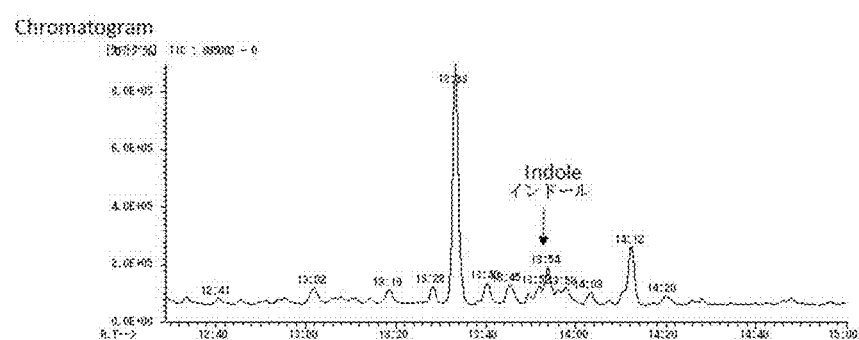
FIG. 3 GC-MS chromatogram in bamboo charcoal administration group

FUNCTIONAL FOOD

CROSS-REFERENCE TO RELATED APPLICATIONS

This patent application is a continuation from the international patent application PCT/JP/2019/017654 filed on Apr. 25, 2019 and now published as WO 2019/235099, which claims priority from the Japanese Patent Application No. 2018-109371 filed on Jun. 7, 2018. The disclosure of each of the above-identified patent applications is incorporated herein by reference.

TECHNICAL FIELD

The present invention relates to a functional food, and in particular, to a functional food having an effect of improving and repressing obesity.

RELATED ART

Now that the society has recently been reputed to be increasingly affluent in a period of sumptuous lifestyle, obesity has become a big social problem as symbolized by metabolic syndrome. Obesity is also regarded as a factor of metabolic diseases and closely associated with coronary heart disease, hypertension, type 2 diabetes, cancer, respiratory complication, and arthrosteitis. Moreover, as even children suffer from obesity these days, growing pediatric obesity is another big problem in the society.

Common obesity treatments are dietetics, exercise therapy, behavioral therapy, and pharmacotherapy, but the main pillars are dietetics and exercise therapy, and the one is generally accompanied by the other. With perseverance required for dietetics and exercise therapy, many patients tend to abandon their attempt to continue these therapies and the attempt often ends up in failure.

In response, many types of drugs, supplements and health food for obesity treatment are being proposed. Supplements and health food advertised as providing an effect of improving and repressing obesity, in particular, are readily ingested and widely available.

Meanwhile, the conventional practice of eating charcoal is believed to be healthy. This is illustrated in Japanese Pharmacopoeia, which classifies medicinal charcoal as antidiarrheal and antiflatulent (Non-Patent Documents 1 and 2). In addition, many types of health food using charcoal have recently been proposed, and some of them are advertised as having health-promoting effects by combining charcoal and dietary fibers to remove enteral waste products and cure constipation.

CITATION LIST

Non-Patent Document 1: the 17th Revised Japanese Pharmacopoeia (Notification No. 64 by the Ministry of Health, Labour and Welfare published on Mar. 7, 2016)
Non-Patent Document 2: Drug Interview Form, Nichi-Iko Pharmaceutical Co., Ltd., "Medicinal Charcoal", Japan Standard Commodity Classification Number: 872319

SUMMARY OF THE INVENTION

Technical Problem

However, no charcoal is actually effective in improving and repressing obesity. In addition, adsorption of enzymes, vitamins, and mineral matter by medicinal charcoal can hinder digestion to cause indigestion, and their long-term use can lead to malnutrition.

Thus, to solve the above problems, the present invention has an object to provide a functional food that utilizes health-promoting effects of charcoal, is readily ingested, has no adverse side effect, and has an effect of improving and repressing obesity.

Solution to the Problem

To solve the aforementioned problem, inventors of the present invention have carried out an extended investigation to find an effect of improving and repressing obesity in food including a composition of a bamboo charcoal and a Bincho charcoal, and an activated bamboo charcoal and an activated Bincho charcoal by examining health-promoting effects of these charcoals. Based on that technique, the present invention was accomplished.

That is, the functional food according to the present invention, according to claim 1, has an effect of improving and repressing obesity, including a charcoal composition composed of at least one of a bamboo charcoal, a Bincho charcoal, an activated bamboo charcoal and an activated Bincho charcoal, in which both of the activated bamboo charcoal and the activated Bincho charcoal have a bulk density of 0.3 to 0.6 g/ml, an average particle diameter of 10 μm or less, a BET specific surface area of 1000 to 1200 m$^2$/g, and an iodine adsorption amount of 1000 to 1300 mg/g.

Also, the present invention, according to claim 2, provides the functional food according to claim 1, in which the charcoal composition is composed of a mixture of a bamboo charcoal or an activated bamboo charcoal and an activated Bincho charcoal.

In addition, the present invention, according to claim 3, provides the functional food according to claim 2, in which a charcoal composition composed of (that is, includes) a mixture of the activated bamboo charcoal and the activated Bincho charcoal has a weight ratio of the activated bamboo charcoal to the activated Bincho charcoal of 1:1.

Also, the present invention, according to claim 4, provides the functional food according to any one of claims 1 to 3, in which the effect of improving and repressing obesity develops contemporaneously with occurrence of the loss of weight in the body.

Moreover, the present invention, according to claim 5, provides the functional food according to any one of claims 1 to 3, in which the effect of improving and repressing obesity develops as decreases in ratio of white adipocytes to the body weight.

Also, the present invention, according to claim 6, provides the functional food according to any one of claims 1 to 3, in which the effect of improving and repressing obesity develops as increases in HDL cholesterol level.

Further, the present invention, according to claim 7, provides the functional food according to any one of claims 1 to 3, in which reduction in AST (GOT) and ALT (GPT) as liver function values in the blood develops as a secondary effect.

Also, the present invention, according to claim 8, provides the functional food according to any one of claims 1 to 3, in which reduction in creatinine and urea nitrogen as renal function values in the blood develops as a secondary effect.

In addition, the present invention, according to claim 9, provides the functional food according to any one of claims 1 to 3, in which the value of A/G (albumin/globulin) ratio in the blood showing the nutritional status, which is almost the same as in a normal meal, develops as a secondary effect.

Also, the present invention, according to claim 10, provides the functional food according to any one of claims 1 to 3, in which an intestinal flora that is kept in a favorable composition develops as a secondary effect.

Additionally, the present invention, according to claim 11, provides the functional food according to any one of claims 1 to 3, in which adsorption of indole as a component of stool odor develops as a secondary effect.

Also, the present invention, according to claim 12, provides the functional food according to any one of claims 1 to 3, in which adsorption of bile acid develops as a secondary effect.

Advantageous Effects of Invention

According to the above configuration, the functional food according to the present invention includes a charcoal composition composed of (includes) at least one of a bamboo charcoal, a Bincho charcoal, an activated bamboo charcoal and an activated Bincho charcoal. Also, both of the activated bamboo charcoal and the activated Bincho charcoal have a bulk density of 0.3 to 0.6 g/ml, an average particle diameter of 10 μm or less, a BET specific surface area of 1000 to 1200 $m^2/g$, and an iodine adsorption amount of 1000 to 1300 mg/g. Thus, the functional food according to the present invention provides an effect of improving and repressing obesity.

Also, according to the above configuration, the charcoal composition may include a mixture of the bamboo charcoal or the activated bamboo charcoal and the activated Bincho charcoal. According to the above configuration, the above operational advantage can more efficiently be provided.

In addition, according to the above configuration, a charcoal composition composed of a mixture of the bamboo charcoal or the activated bamboo charcoal and the activated Bincho charcoal may have a weight ratio of the bamboo charcoal or the activated bamboo charcoal to the activated Bincho charcoal of 1:1. According to the above configuration, the above operational advantage can more efficiently be provided.

Also, according to the above configuration, an effect of improving and repressing obesity develops as body weight loss, decreases in ratio of white adipocytes to the body weight, and increases in HDL cholesterol level. Also, according to the above configuration, secondary effects of the effect of improving and repressing obesity develop as reduction in AST (GOT) and ALT (GPT) as liver function values in the blood, reduction in creatinine and urea nitrogen as renal function values in the blood, the value of A/G (albumin/globulin) ratio in the blood showing the nutritional status, which is almost the same as in a normal meal, an intestinal flora that is kept in a favorable composition, adsorption of indole as a component of stool odor, and adsorption of bile acid.

Thus, according to the above configuration, the present invention can provide a functional food that utilizes health-promoting effects of charcoal, is readily ingested, has no adverse side effect, and has an effect of improving and repressing obesity.

BRIEF DESCRIPTION OF THE DRAWINGS

FIG. 9 is a chart showing a CG-MS chromatogram of a bamboo charcoal administration group in Example 2.

DETAILED DESCRIPTION

Figure 1:
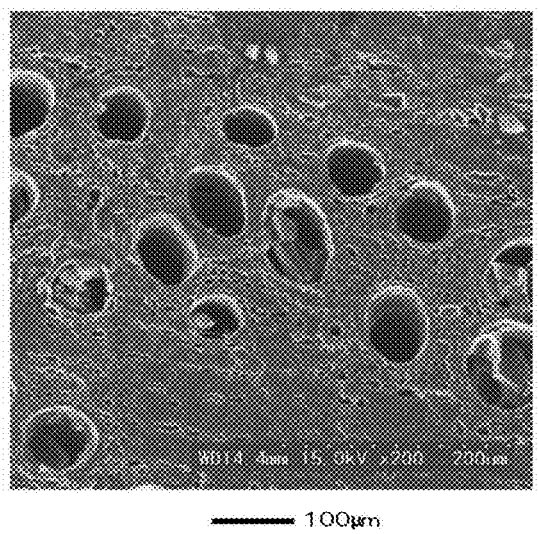
FIG. 1 is an electron micrograph showing a bamboo charcoal prepared in this embodiment in the duct direction.

The present invention will be described with reference to embodiments. The present invention is not restricted to the following embodiments only. First, inventors of the present invention prepared a bamboo charcoal, a Bincho charcoal, an activated bamboo charcoal and an activated Bincho charcoal, and using these charcoals, their fundamental health-promoting effects were confirmed.

<Preparation of Bamboo Charcoal>

A quarter-divided moso bamboo was placed in a stainless carbonizer, heated for many hours, and finally carbonized at 700 to 900° C. (900° C. in this embodiment). In this embodiment, a low-temperature carbonized bamboo charcoal carbonized at a low-temperature of 300° C. was also prepared. The bamboo charcoal prepared in this embodiment is several centimeters in size, and the BET specific surface area (specific surface area measured by a BET equation) was 100 to 400 $m^2/g$.

<Preparation of Bincho Charcoal>

Selectively-cut *Quercus phillyraeoides* is bundled in several pieces, and the resulting bundles are arranged to stand from the back of a kiln (setting in a kiln). After setting the bundles in the kiln, more than half of a kiln opening is filled with clay and stones, and miscellaneous trees are supplied as fuel at the lower part of the kiln to set fire (opening firing). Upon opening firing, moisture-containing white smoke initially comes out of the kiln one after another, and the smoke emits strong acid odor. After checking the color and odor of the smoke, several small holes are left and all the remaining kiln openings are filled, and steamed and charred for about one week to 10 days (carbonization). The kiln temperature is maintained at a low temperature of approx. 300° C. After carbonization, the kiln opening is slowly opened to feed air, and the bark of charcoal materials is charred and allowed to glow (refinement). The kiln temperature reached 800 to 1200° C. (1200° C. in this embodiment). After refinement, the charcoals are gradually removed out of the kiln from the closest one, and they are slowly cooled by adding decarbonized coal ash thereto. Bincho charcoals are classified into cut log, half log, thin log, small log, upper small log and the like according to the size or shape. The BET specific surface area of Bincho charcoals prepared in this embodiment was 50 to 200 $m^2/g$.

<Preparation of Activated Charcoal>

The bamboo charcoal and the Bincho charcoal prepared as described above were each activated as below. First, the bamboo charcoal or the Bincho charcoal were granulated into 5 mm or less by a coarse crusher such as jaw crusher or roll crusher. Then, coarse-crushed bamboo charcoal and Bincho charcoal were fed into a rotary kiln capable of uniform treatment by rotating the kiln, and the temperature was maintained at 800° C. to 1000° C. (900° C. in this embodiment) to activate the charcoals for a predetermined time by introducing a predetermined amount of steam from one side of the kiln. Thereafter, the charcoals were crushed by a fine pulverizer such as ball mill or jet mill and then screened to produce fine powders 10 μm or less. Table 1 shows the properties of the activated bamboo charcoal and the activated Bincho charcoal obtained in comparison with a commercially available activated charcoal. In addition, the iodine adsorption amount was measured by the method according to JIS K-1474 (2014).

TABLE 1

|  | Activated temperature (° C.) | Activated yield (%) | Iodine adsorption amount (mg/g) | BET specific surface area (m²/g) |
|---|---|---|---|---|
| Activated bamboo charcoal | 900 | 42 | 1160 | 1070 |
| Activated Bincho charcoal | 900 | 53 | 1080 | 1010 |
| Commercially available activated charcoal | — | — | 955 | 990 |

Figure 2:
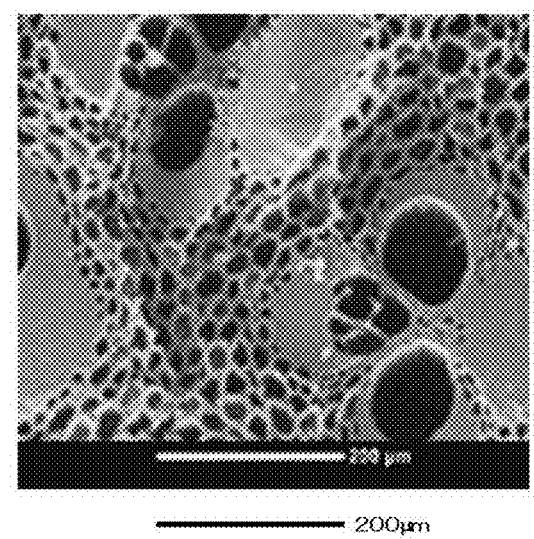
FIG. 2 is an electron micrograph showing the bamboo charcoal in FIG. 1 in the lateral direction of the duct.
Figure 3:
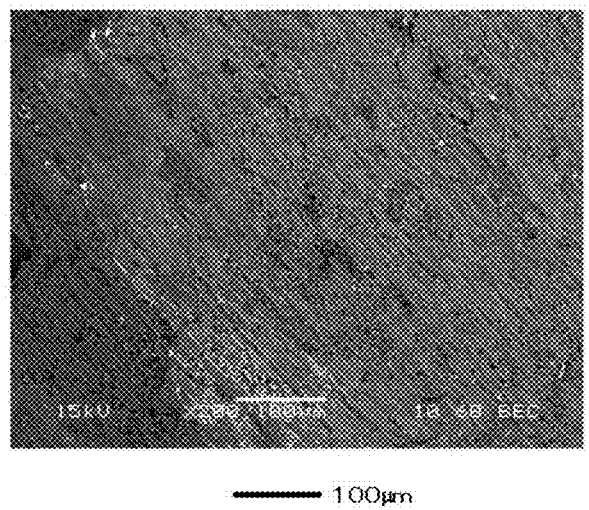
FIG. 3 is an electron micrograph showing a Bincho charcoal prepared in the present invention.
Figure 4:
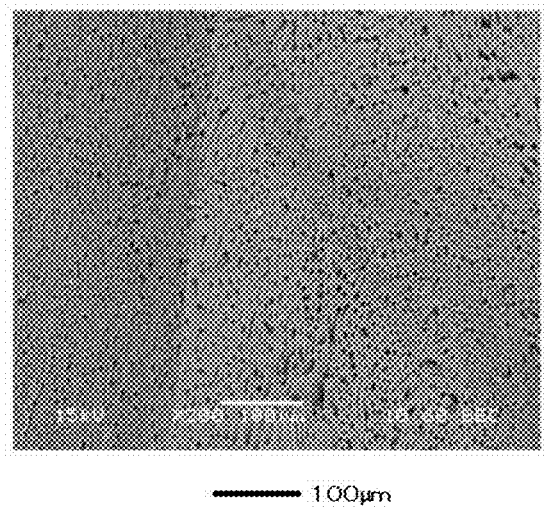
FIG. 4 is an electron micrograph showing a commercially available activated charcoal.

FIGS. 1 to 6 shows electron micrographs of the charcoals prepared as described above. FIG. 1 is an electron micrograph showing a bamboo charcoal prepared in this embodiment in the duct direction. FIG. 2 is an electron micrograph showing the bamboo charcoal in FIG. 1 in the lateral direction of the duct. FIG. 3 is an electron micrograph showing a Bincho charcoal prepared in this embodiment. Also, FIG. 4 is an electron micrograph showing a commercially available activated charcoal. With reference to FIGS. 1 to 4, the bamboo charcoal and the Bincho charcoal have larger pores than the commercially available activated charcoal.

Figure 5:
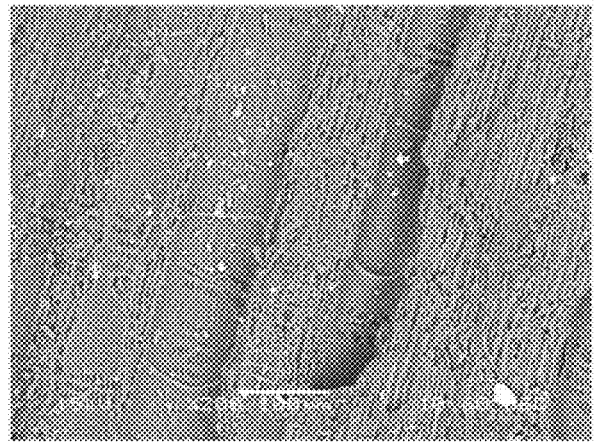
FIG. 5 is an electron micrograph showing an activated Bincho charcoal prepared in this embodiment.
Figure 6:
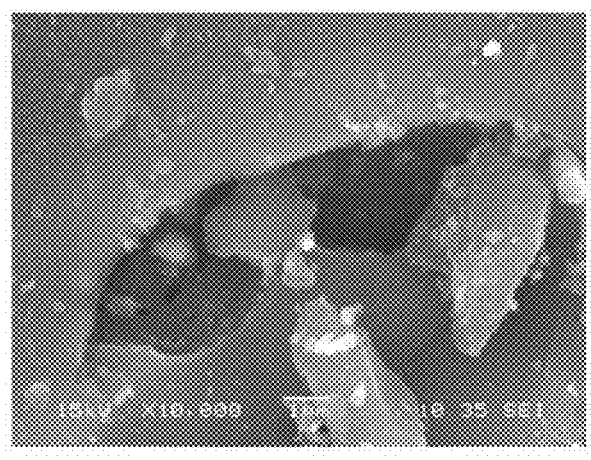
FIG. 6 is an electron micrograph showing the activated Bincho charcoal in FIG. 5 enlarged.

Meanwhile, FIG. 5 is an electron micrograph showing an activated Bincho charcoal prepared in this embodiment. Also, FIG. 6 is an electron micrograph showing the activated Bincho charcoal further enlarged. In the activated Bincho charcoal are observed micropores formed by activation.

Then, using the bamboo charcoal, the Bincho charcoal, the activated bamboo charcoal and the activated Bincho charcoal thus prepared, an effect of improving and repressing obesity and health-promoting effects developing as secondary effects were confirmed by referring to each of the Examples by examining how effective the type of charcoal composition is. Specifically, the function of repressing body weight gain developing as an operational effect was confirmed. As health-promoting effects developing as secondary effects were confirmed AST (GOT) and ALT (GPT) liver function values in the blood, creatinine and urea nitrogen renal function values in the blood, A/G (albumin/globulin) ratio in the blood showing the nutritional status, changes in compositions of an intestinal flora, indole adsorption function as a stool odor component, and bile acid adsorption function. The present invention is not restricted to the following examples only.

Example 1

<Function of Repressing Body Weight Gain>

In this example 1, high-fat diet and charcoal-added feed were orally administered to rats and they were reared for 2 weeks to confirm the effect of charcoal added to the feed on the body weight gain. Also, this Example 1 confirmed the function of repressing the body weight gain only for a bamboo charcoal (carbonization temperature: 900° C.) and a Bincho charcoal as preliminary discussion. Table 2 shows the details of the feed provided for rats in each group.

TABLE 2

| Group | | Details of feed |
|---|---|---|
| Comparative Example 1-1 | Normal meal (control) | Normal meal (MF, Product from Oriental Yeast Co., ltd.) |
| Comparative Example 1-2 | High-fat diet | Normal meal + sunflower oil 10 (V/W) % |
| Example 1-1 | High-fat diet + bamboo charcoal | Normal meal + sunflower oil 10 (V/W) % + charcoal 10(V/W) % |
| Example 1-2 | High-fat diet + Bincho charcoal | Normal meal + sunflower oil 10 (V/W) % + charcoal 10(V/W) % |

After the rats were reared with the above feed for 2 weeks, the body weight was measured before, and 7 and 14 days after the feed was given. The feces after administering the charcoal was found to change the color to black from 16 hours after the administration. Since there is no difference in feed intake among all the groups, there seems to be no effect of charcoal on the ingestion.

Figure 7:
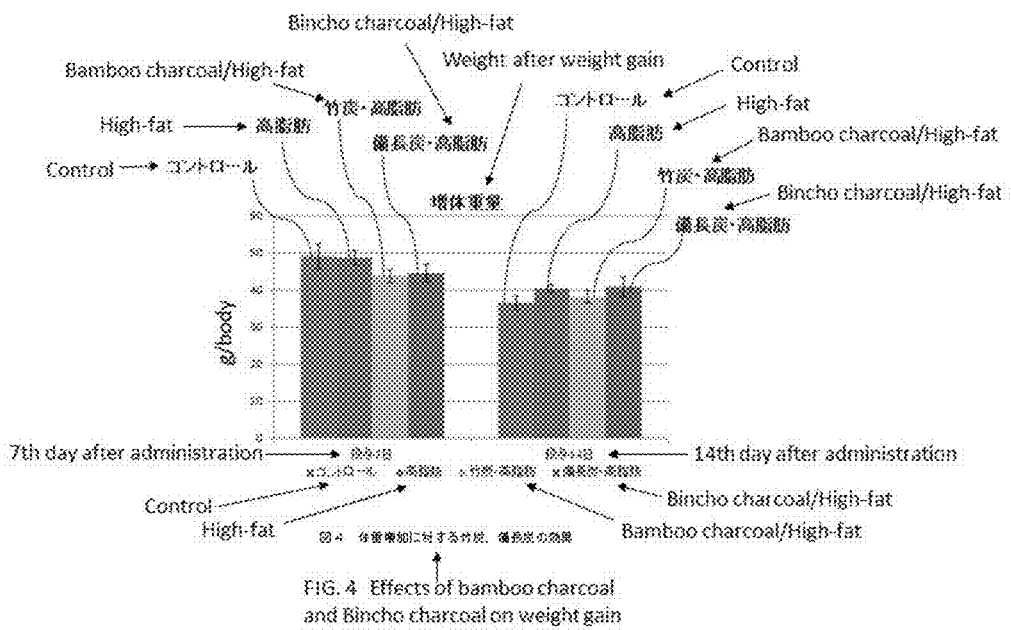
FIG. 7 is a graph showing increases in body weight in a bamboo charcoal administration group and a Bincho charcoal administration group in Example 1.

FIG. 7 is a graph showing increases in body weight in a bamboo charcoal administration group and a Bincho charcoal administration group in this Example 1. In FIG. 7, a comparison of the body weight and body weight gain amount 7 days after administering the high-fat diet found repression of the body weight gain in both of the bamboo charcoal administration group (Example 1-1) and the Bincho charcoal administration group (Example 1-2), more than in the high-fat diet administration group (Comparative Example 1-2) and the control group (Comparative Example 1-1). In the bamboo charcoal administration group (Example 1-1), the body weight gain was repressed even on the 14th day more than in the high-fat diet administration group (Comparative Example 1-2).

Example 2

In this Example 2, health-promoting effects developing as secondary effects of an effect of improving and repressing obesity were confirmed. The secondary effects confirmed in this Example 2 are liver function values in the blood, renal function values in the blood, the A/G ratio in the blood showing the nutritional status, changes in intestinal flora composition, and indole adsorption function. Each of the items will be described as follows.

<Liver Function Values in the Blood>

Herein, AST (GOT) and ALT (GPT) as liver function values in the blood were confirmed regarding health-promoting effects developing as secondary effects of the effect of improving and repressing obesity. These values are effective as indexes of the liver function.

AST (asparate aminotransferase) is a type of enzyme referred to as GOT (glutamic oxaloacetic transaminase), and is contained in many types of organ tissue cells such as liver, skeletal muscles, cardiac muscles, kidneys, and red blood cells. Meanwhile, ALT (Alanine transaminase), referred to as GPT (glutamic pyruvic transaminase), is a type of enzyme for interconversion of pyruvic acid and glutamic acid into alanine and α-ketoglutaric acid.

AST (GOT) is referred to as deviation enzyme, and when a tissue is damaged, AST in a tissue comes out of a cell and flows into the blood. Thus, when an organ containing ASTs in large quantities (liver, heart, skeletal muscle, red blood cell and the like) is damaged, the values in the blood increase. Since AST (GOT) is present in large quantities in non-liver tissues, patients having a high value only in AST are diagnosed as possibly having skeletal muscle disease or blood disease other than liver disease, and patients having high values both in AST and ALT or ALT (GPT) alone are diagnosed as possibly having liver disease.

In order to confirm the effect of charcoal ingestion on the liver function, each group of 5 mice was reared with feed composed of high-fat diet added with a bamboo charcoal (carbonization temperature: 900° C.), a low-temperature carbonized bamboo charcoal (carbonization temperature: 300° C.), an activated bamboo charcoal (activated temperature: 900° C.), a Bincho charcoal, and an activated Bincho charcoal (activated temperature: 900° C.). The trial subjects were 7-week old mice (ICR, male), which were tamed and reared for one week and the trial started from the 8th week. The mice were each reared in separate cages. Table 3 shows the details of the feed given to the mice in each group.

TABLE 3

| Group | | Details of feed |
|---|---|---|
| Comparative Example 2-1 | Normal meal (control) | Normal meal (MF, Product from Oriental Yeast Co., ltd.) |
| Comparative Example 2-2 | High-fat diet | Normal meal + sunflower oil 10 (V/W) % |
| Example 2-1 | High-fat diet + bamboo charcoal | Normal meal + sunflower oil 10 (V/W) % + charcoal 10(V/W) % |
| Example 2-2 | High-fat diet + low-temperature carbonized bamboo charcoal | Normal meal + sunflower oil 10 (V/W) % + charcoal 10 (V/W) % |
| Example 2-3 | High-fat diet + activated bamboo charcoal | Normal meal + sunflower oil 10 (V/W) % + charcoal 10 (V/W) % |
| Example 2-4 | High-fat diet + Bincho charcoal | Normal meal + sunflower oil 10 (V/W) % + charcoal 10 (V/W) % |
| Example 2-5 | High-fat diet + activated Bincho charcoal | Normal meal + sunflower oil 10 (V/W) % + charcoal 10 (V/W) % |

Table 4 shows AST (GOT) and ALT (GPT) values as a result of a blood test on mice reared for 2 weeks.

TABLE 4

| Group | | AST(GOT) (U/L) | ALT(GPT) (U/L) |
|---|---|---|---|
| Comparative Example 2-1 | Normal meal (control) | 89.6 | 18.0 |
| Comparative Example 2-2 | High-fat diet | 86.2 | 17.4 |
| Example 2-1 | High-fat diet + bamboo charcoal | 71.0 | 14.0 |
| Example 2-2 | High-fat diet + low-temperature carbonized bamboo charcoal | 80.4 | 15.6 |
| Example 2-3 | High-fat diet + activated bamboo charcoal | 57.2 | 14.0 |
| Example 2-4 | High-fat diet + Bincho charcoal | 53.2 | 15.8 |
| Example 2-5 | High-fat diet + activated Bincho charcoal | 83.4 | 16.6 |

In Table 4, the AST (GOT) and ALT (GPT) values were lower in all the charcoal administration groups (Examples 2-to 2-5) than in the high-fat diet administration group (Comparative Example 2-2) and the control group (Comparative Example 2-1). Accordingly, no liver disease is observed in the charcoal administration groups, and the group mice show favorable state of the liver function.

<Renal Function Values in the Blood>

Then, creatinine and urea nitrogen as renal function values in the blood were confirmed regarding health-promoting effects developing as secondary effects of an effect of improving and repressing obesity. These values are effective as indexes of the renal function.

Creatinine (Cr) is one of the waste products after creatine (a type of amino acid) in the muscle is used as energy for working muscles. A certain amount of creatinine is constantly produced regardless of food, rarely reabsorbed into the body, and eliminated only from the kidneys. Thus, creatinine can be regarded as an index of the renal function. This is attributed to increases in creatinine when decline in the renal function allows creatinine not to be eliminated from the kidneys and to stay in the blood.

Meanwhile, urea nitrogen (BUN) is a waste product of proteins (final metabolite of protein) consumed as energy in the body. The protein is decomposed inside the body to be ammonia. As a harmful substance in the human body, the ammonia is metabolized in the liver to be converted into non-toxic urea. Urea is filtered at the glomerulus in the kidneys, and eliminated into urea, but part thereof is reabsorbed at the convoluted tubule to get back into the blood. Thus, urea nitrogen can be regarded as an index of the renal function. This is attributed to increases in urea nitrogen level when decline in the renal function allows urea nitrogen not to be eliminated from the kidneys and to stay in the blood.

In order to confirm the effect of charcoal ingestion on the renal function, a trial started on the 8-week old mice reared with the feed described in the above Table 3. Table 5 shows creatinine (Cr) and urea nitrogen (BUN) values as a result of a blood test on mice reared for 2 weeks after the trial starts.

TABLE 5

| Group | | Creatinine (mg/dl) | Urea nitrogen (mg/dl) |
|---|---|---|---|
| Comparative Example 2-1 | Normal meal (control) | 0.118 | 32.8 |
| Comparative Example 2-2 | High-fat diet | 0.114 | 36.0 |
| Example 2-1 | High-fat diet + bamboo charcoal | 0.100 | 29.4 |
| Example 2-2 | High-fat diet + low-temperature carbonized bamboo charcoal | 0.084 | 23.8 |
| Example 2-3 | High-fat diet + activated bamboo charcoal | 0.080 | 24.0 |
| Example 2-4 | High-fat diet + | 0.085 | 23.6 |

TABLE 5-continued

| Group | | Creatinine (mg/dl) | Urea nitrogen (mg/dl) |
|---|---|---|---|
| Example 2-5 | Bincho charcoal High-fat diet + activated Bincho charcoal | 0.092 | 27.8 |

In Table 5, the creatinine (Cr) and urea nitrogen (BUN) values were lower in all the charcoal administration groups (Examples 2-1 to 2-5) than in the high-fat diet administration group (Comparative Example 2-2) and the control group (Comparative Example 2-1). Accordingly, the kidneys normally function in the charcoal administration group and creatinine and urea nitrogen are eliminated out of the body as urine, and their amounts in the blood decline. These low values indicate that the kidneys normally function.

<A/G Ratio in the Blood Showing the Nutritional Status>

Then, the A/G (albumin/globulin) ratio in the blood showing the nutritional status was confirmed regarding health-promoting effects developing as secondary effects of an effect of improving and repressing obesity. There are approx. 100 types of proteins in the serum. In a healthy subject, albumin accounts for about 67% of the total proteins in the serum. Since the albumin is produced only in the liver, any liver disorder significantly declines albumin's measured values.

On the other hand, what accounts for another about 33% is globulin. The globulin is produced by organs called as lymphatic tissue such as lymph nodes, intestinal tracts, and bone marrows, in addition to the liver. Thus, the ratio of albumin to globulin (A/G ratio) is a simple index showing abnormality of the liver or the like. The standard human A/G ratio is 1.0 to 2.3. Thus, the A/G ratio can be regarded as an index of health status.

In order to confirm the effect of charcoal ingestion on the health status, a trial started on the 8-week old mice reared with the feed described in the above Table 3. Table 6 shows A/G ratios as a result of a blood test on mice reared for 2 weeks after the trial starts.

TABLE 6

| Group | | A/G ratio |
|---|---|---|
| Comparative Example 2-1 | Normal meal (control) | 1.712 |
| Comparative Example 2-2 | High-fat diet | 1.634 |
| Example 2-1 | High-fat diet + bamboo charcoal | 1.624 |
| Example 2-2 | High-fat diet + low-temperature carbonized bamboo charcoal | 1.488 |
| Example 2-3 | High-fat diet + activated bamboo charcoal | 1.656 |
| Example 2-4 | High-fat diet + Bincho charcoal | 1.666 |
| Example 2-5 | High-fat diet + activated Bincho charcoal | 1.750 |

In reference to Table 6, A/G ratio values in all the charcoal administration groups (Examples 2-1 to 2-5) were substantially the same level as that corresponding to the high-fat diet administration group (Comparative Example 2-2) and the control group (Comparative Example 2-1). Accordingly, with no adverse effect on the health of the mice even in the charcoal administration group, the mice show no symptoms such as malnutrition, hypoproteinemia, liver disorder, kidney disorder, and protein-losing gastrointestinal symptom.

<Changes in Composition of Intestinal Flora>

Then, the intestinal flora composition was confirmed regarding health-promoting effects developing as secondary effects of an effect of improving and repressing obesity. Generally, when high-fat diet is ingested instead of a normal meal, the intestinal flora composition changes, leading to unhealthy conditions. Even when high-fat diet is ingested together with a charcoal composition, the intestinal flora composition can preferably be maintained as in the normal meal.

In order to confirm the above advantage, each group of 5 mice was reared with the feed described in the above Table 3 for 13 days.

The intestinal flora was analyzed using mouse cecotrope by collecting 2 samples from each of the control group and the high-fat diet administration group and 3 samples from the charcoal administration group. DNA was extracted from the feces using QIAamp DNA Stool Mini (Qiagen). The DNA amount was quantitated by Nano Drop. The intestinal flora was analyzed by the next-generation sequencer Miseq (Illumina, Inc.). Each of the feces used was approx. 300 mg. The DNA amount showed significant differences among the groups, and these DNAs ware analyzed by the next-generation sequencer. Table 7 shows intestinal flora compositions (%) as a result of the intestinal flora analysis.

TABLE 7

| | Intestinal flora | | | |
|---|---|---|---|---|
| | Bacteroidetes (%) | Deferribacteres (%) | Firmicutes (%) | Proteobacteria (%) |
| Comparative Example 2-1 | 51.1 | 1.6 | 40.7 | 6.6 |
| Comparative Example 2-2 | 36.8 | 2.4 | 54.1 | 6.7 |
| Example 2-1 | 41.4 | 2.3 | 49.0 | 7.3 |
| Example 2-2 | 45.6 | 4.0 | 41.2 | 9.2 |
| Example 2-3 | 49.4 | 2.3 | 40.8 | 7.5 |
| Example 2-4 | 47.0 | 1.4 | 45.2 | 6.4 |
| Example 2-5 | 39.1 | 4.6 | 46.1 | 10.2 |

In Table 7, there were considerable differences in the intestinal flora composition between the high-fat diet administration group (Comparative Example 2-2) and the charcoal-added high-fat diet feed administration groups (Examples 2-1 to 2-5). While the Firmicutes phylum rate in the high-fat diet ingestion group (Comparative Example 2-2) was higher than in the high-fat diet non-ingestion control group (Comparative Example 2-1), the flora level was substantially close to that in the control group (Comparative Example 2-1) although the mice in the were considerable charcoal-added high-fat diet feed administration groups (Examples 2-1 to 2-5) ingested high-fat diet. Accordingly, charcoal ingestion maintains the intestinal flora with a favorable composition, that is the composition of intestinal flora present as a result of consumption of the functional food is maintained substantially unchanged in comparison with that present when a normal meal (that is a regular diet, as defined by related art) is consumed.

<Indole Absorption Function>

Then, the indole absorption function was confirmed regarding health-promoting effects developing as secondary effects of an effect of improving and repressing obesity. Generally, illustrative example of a stool odor component includes hydrogen sulfide, ammonia, skatole, indole, and amine, and these substances are taken in the blood to allegedly cause constipation, rough skin, or even cancer and aging. Thus, whether the charcoal composition functions to absorb indole in the body was confirmed by focusing on the indole as a main stool odor component.

In order to confirm the above advantage, each group of 5 mice was reared with the feed described in the above Table 3 for 13 days.

The stool odor component was extracted using a silica monolith scavenger (MnotTap DCC18 (GL Sciences Inc.). Specifically, approx. 300 mg of the feces was measured in a sample bottle, one MnotTap DCC18 was set therein, the stool odor was adsorbed by headspace method at 60° C. for 3 hours, the components were extracted by dichloromethane, and analyzed by GC-MS (JMS-QI050GC).

Figure 8:
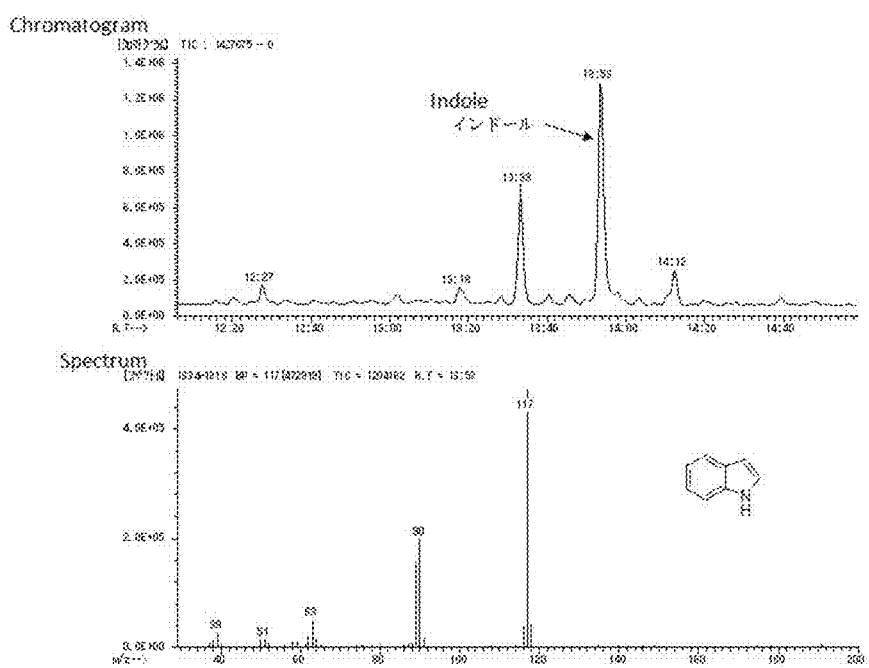
FIG. 8 is a chart showing GC-MS chromatogram and indole MS fragment in the analysis of the indole amount in the control group in Example 2.

FIG. 8 is a chart showing GC-MS chromatogram and indole MS fragment in the analysis of the indole amount in the control group (Comparative Example 2-1). In FIG. 8, the indole peak is considerably shown at the retention time of 13.53, indicating strong feces/stool odor. In a high-fat diet group (Comparative Example 2-2, not shown), a chromatogram whose component is significantly different from the control group (Comparative Example 2-1) was obtained, but the indole peak was considerably shown.

Meanwhile, the relative intensity of indole significantly decreased in all the charcoal administration groups (Examples 2-1 to 2-5), FIG. 9 is a chart showing one example of CG-MS chromatogram in the bamboo charcoal administration group (Example 2-1). Also, Table 8 shows GC peak area values of indole in each of the Comparative Examples and Examples.

TABLE 8

| Group | | GC peak area of indole (×10$^5$) |
|---|---|---|
| Comparative Example 2-1 | Normal meal (control) | 39.5 |
| Comparative Example 2-2 | High-fat diet | 18.1 |
| Example 2-1 | High-fat diet + bamboo charcoal | 3.6 |
| Example 2-2 | High-fat diet + low-temperature carbonized bamboo charcoal | 3.6 |
| Example 2-3 | High-fat diet + activated bamboo charcoal | 11.1 |
| Example 2-4 | High-fat diet + Bincho charcoal | 1.1 |
| Example 2-5 | High-fat diet + activated Bincho charcoal | 1.1 |

In Table 8, the GC peak area of indole significantly decreased in all the charcoal administration groups (Examples 2-1 to 2-5). In particular, the indole peak practically disappears (within an experimental error) in the Bincho charcoal administration group (Example 2-4) and the activated Bincho charcoal administration group (Example 2-5). Accordingly, charcoal ingestion adsorbs indole as a main stool odor component in the body and eliminate indole out of the body together with the charcoal.

Example 3

Then, this Example 3 confirms the function of repressing the body weight gain by synergetic effect by combining 2 types of charcoals, and other health-promoting effects. Specifically, the weight variation, repression of increasing white adipocytes, increases in HDL cholesterol level (good cholesterol level), AST (GOT), ALT (GPT), ALP, decline in urea nitrogen, increases in phospholipids, A/G ratio, the effect of mixed charcoal on the total bile acid were confirmed.

In order to confirm these properties, a charcoal composition in which a bamboo charcoal and an activated Bincho charcoal are mixed such that the weight ratio is 1:1 (hereinafter referred to as "mixed charcoal") was used in this Example 3. The experimental animals were 4-week old mice (ICR, male), which were tamed and reared for one week and a trial started from the 5th week by administering a high-fat diet (High Fat Diet 32, Product from CLEA Japan, Inc.) and the mice were reared until the 8th week. Thereafter, the mice were reared for 4 weeks with solidified feed composed of a normal meal (CLEA Rodent Diet CE-2, Product from CLEA Japan, Inc.) added with a mixed charcoal (bamboo charcoal: activated Bincho charcoal=1:1) by 1.0% and 0.1%. Each group of 5 mice was reared. Table 9 shows the details of the feed given to the mice in each group.

TABLE 9

| Group | | Details of feed |
|---|---|---|
| Comparative Example 3-1 | Normal meal (control) | Normal meal (CLEA Rodent Diet CE-2, Product from CLEA Japan, Inc.) |
| Comparative Example 3-2 | High-fat diet | High-fat diet (High Fat Diet 32, Product from CLEA Japan, Inc.) |
| Example 3-1 | High-fat diet + mixed charcoal 0.1% | (High-fat diet, 8 weeks) + (normal meal + charcoal composition, 4 weeks) |
| Example 3-2 | High-fat diet + mixed charcoal 1.0% | (High-fat diet, 8 weeks) + (normal meal + charcoal composition, 4 weeks) |

<Function of Repressing Body Weight Gain>

Table 10 shows the weight variation (%) one week after adding a mixed charcoal on the basis of the body weight of the mice reared for 8 weeks with feed including no mixed charcoal added.

TABLE 10

| Group | | Weight variation (%) |
|---|---|---|
| Comparative Example 3-1 | Normal meal (control) | 4.1 |
| Comparative Example 3-2 | High-fat diet | 0 |
| Example 3-1 | High-fat diet + mixed charcoal 0.1% | −0.8 |
| Example 3-2 | High-fat diet + mixed charcoal 1.0% | −3.2 |

In Table 10, both of the mixed charcoal-added feed administration groups (Example 3-1, Example 3-2) show a negative weight variation to repress the body weight gain. The effect was significant, particularly in the mixed charcoal 1.0%-added feed administration group (Example 3-2).

<Repression of Increasing White Adipocytes>

A white adipocyte functions to accumulate extra calories in the body as a neutral fat. White adipocytes are found all over the body, particularly in the hypogastrium, buttocks, thighs, dorsum, the top of forearms, and around the viscus. Table 11 shows the weight ratio (W/W %) of white adipocytes to the body weight 4 weeks after adding a mixed charcoal.

TABLE 11

| Group | | White adipocyte/weight (W/W %) |
|---|---|---|
| Comparative Example 3-1 | Normal meal (control) | 1.32 |
| Comparative Example 3-2 | High-fat diet | 2.24 |
| Example 3-1 | High-fat diet + mixed charcoal 0.1% | 1.52 |
| Example 3-2 | High-fat diet + mixed charcoal 1.0% | 1.62 |

In Table 11, both of the mixed charcoal-added feed administration groups (Example 3-1, Example 3-2) show lower weight ratios of white adipocytes (W/W %) than the high-fat diet administration group (Comparative Example 3-2), and almost the same values as the control group (Comparative Example 3-1). Thus, obesity is repressed.

<HDL Cholesterol Level>

HDL cholesterol functions to transport extra cholesterol in the blood to the liver to inhibit cholesterols increases in the blood. Therefore, HDL cholesterol is referred to as "good cholesterol". Table 12 shows HDL cholesterol values 4 weeks after adding a mixed charcoal.

TABLE 12

| Group | | HDL cholesterol level (mg/dl) |
|---|---|---|
| Comparative Example 3-1 | Normal meal (control) | 68.3 |
| Comparative Example 3-2 | High-fat diet | 53.3 |
| Example 3-1 | High-fat diet + mixed charcoal 0.1% | 60.1 |
| Example 3-2 | High-fat diet + mixed charcoal 1.0% | 61.6 |

In Table 12, both of the mixed charcoal-added feed administration groups (Example 3-1, Example 3-2) show a higher HDL cholesterol level than the high-fat diet administration group (Comparative Example 3-2).

<AST (GOT), ALT (GPT), ALP>

Table 13 shows AST (GOT), ALT (GPT), and ALP values 4 weeks after adding a mixed charcoal.

TABLE 13

| Group | | AST (GOT) (U/L) | ALT (GPT) (U/L) | ALP (U/L) |
|---|---|---|---|---|
| Comparative Example 3-1 | Normal meal (control) | 120.2 | 37.7 | 167.1 |
| Comparative Example 3-2 | High-fat diet | 132.0 | 33.7 | 171.9 |
| Example 3-1 | High-fat diet + mixed charcoal 0.1% | 86.9 | 23.0 | 133.9 |
| Example 3-2 | High-fat diet + mixed charcoal 1.0% | 98.0 | 25.7 | 146.6 |

In Table 13, both of the mixed charcoal-added feed administration groups (Example 3-1, Example 3-2) show lower AST (GOT), ALT (GPT), and ALP values than the high-fat diet administration group (Comparative Example 3-2) and the control group (Comparative Example 3-1), indicating normal liver function.

<Values of Urea Nitrogen and Phospholipids>

Table 14 shows values of urea nitrogen and phospholipids 4 weeks after adding a mixed charcoal.

TABLE 14

| Group | | Urea nitrogen (mg/dl) | Phospholipid (mg/dl) |
|---|---|---|---|
| Comparative Example 3-1 | Normal meal (control) | 32.0 | 203.3 |
| Comparative Example 3-2 | High-fat diet | 31.0 | 175.0 |
| Example 3-1 | High-fat diet + mixed charcoal 0.1% | 26.9 | 185.3 |
| Example 3-2 | High-fat diet + mixed charcoal 1.0% | 26.4 | 189.3 |

In Table 14, both of the mixed charcoal-added feed administration groups (Example 3-1, Example 3-2) show lower urea nitrogen values than the high-fat diet administration group (Comparative Example 3-2) and the control group (Comparative Example 3-1), indicating normal kidney function. Meanwhile, lack of phospholipids causes cholesterol accumulation in blood vessels, resulting in lifestyle diseases such as arteriosclerosis and diabetes, but both of the mixed charcoal-added feed administration groups (Example 3-1, example 3-2) show higher phospholipids than the high-fat diet administration group (Comparative Example 3-2).

<A/G Ratio and Total Bile Acid Values>

A/G ratio refers to the ratio of albumin to globulin in amount, and is used as a simple method for detecting abnormality of the liver or the like. Albumin is produced in the liver, and if the liver is itself damaged, the albumin level in the blood considerably declines and the A/G ratio also decreases. The A/G ratio declines also in nephrotic syndrome, protein-losing gastroenteropathy, malnutrition, and diabetes. The A/G ratio significantly declines also in inflammation and malignant tumor.

Meanwhile, the total bile acid in the blood cannot be excreted to the intestinal tract in hepatic and biliary tract disorders (such as intrahepatic cholestasis and biliary obstruction), and the bile acid in the blood shows a higher value, but a smaller value in cases where its reabsorption from the small intestine and ileum is impaired. An abnormally high bile acid value can correspond to acute hepatitis, chronic liver disease, biliary stasis, and bacterial overgrowth syndrome, while an abnormally low bile acid value is associated with intestinal malabsorption syndrome.

Table 15 shows A/G ratios and total bile acid values 4 weeks after adding a mixed charcoal.

TABLE 15

| Group | | A/G ratio | Total bile acid (μmol/L) |
|---|---|---|---|
| Comparative Example 3-1 | Normal meal (control) | 1.362 | 4.217 |
| Comparative Example 3-2 | High-fat diet | 1.577 | 5.486 |
| Example 3-1 | High-fat diet + mixed charcoal 0.1% | 1.457 | 3.671 |

TABLE 15-continued

| Group | | A/G ratio | Total bile acid (μmol/L) |
|---|---|---|---|
| Example 3-2 | High-fat diet + mixed charcoal 1.0% | 1.505 | 3.357 |

In Table 15, both of the mixed charcoal-added feed administration groups (Example 3-1, Example 3-2) show higher A/G ratios than the control group (Comparative Example 3-1), and lower A/G ratios than the high-fat diet administration group (Comparative Example 3-2). These values are normal.

Meanwhile, both of the mixed charcoal-added feed administration groups (Example 3-1, Example 3-2) show slightly lower total bile acid amounts in the blood than the control group (Comparative Example 3-1), but such values can be normal.

As stated above, the above Example 3 confirmed that mixed charcoals (bamboo charcoal:activated Bincho charcoal=1:1) have an effect of repressing the body weight gain and other health-promoting effects. Also, these charcoals (incl. mixed charcoal) can orally be ingested readily to obtain each of the above effects.

Example 4

<Function of Adsorbing Bile Acid>

This Example 4 confirmed the function of adsorbing bile acid regarding health-promoting effects developing as secondary effects of an effect of improving and repressing obesity. Generally, cholesterol in the body is converted into bile acid by the liver. The bile acid synthesized from cholesterol by the liver is secreted into the intestinal tract through the bile duct to allow the bile acid to facilitate digestion/absorption of dietary lipid in the small intestine. 95% or more of the secreted bile acid is reabsorbed from the intestinal tract and 5% or less thereof is eliminated out of the body. Adsorption and elimination of the bile acid in the intestinal tract for removal and reabsorption of the bile acid for its circulation repression promote synthesis of new bile acids from the cholesterol. Accordingly, the resulting decline in cholesterol level in the blood can repress fatty liver as well.

In order to confirm this advantage, an adsorption test of bile acid (glycocholic acid) was conducted. Specifically, 0.020 g or 0.0020 g of a charcoal was dispensed into a test tube, then 2 mL of 50 μmol/L bile acid (glycocholic acid) was added thereto, shaken at 37° C. for 30 minutes, and filtered to separate the charcoal and an aqueous solution. Thereafter, the concentration of the bile acid (glycocholic acid) in the separated aqueous solution was measured by the bile acid/Test Wako (Product from FUJIFILM Wako Pure Chemical Corporation, enzyme color test). Table 16 shows the results of the bile acid adsorption test.

TABLE 16

| | Concentration | Bile acid concentration (μmol/L) | | |
|---|---|---|---|---|
| | of charcoal | 0 | 0.10% | 1.00% |
| Comparative Example 4-1 | Control | 50 | — | — |
| Example 4-1 | Bamboo charcoal | — | 48.0 | 26.0 |
| Example 4-2 | Low-temperature carbonized bamboo charcoal | — | 48.3 | 21.0 |

TABLE 16-continued

| | Concentration | Bile acid concentration (μmol/L) | | |
|---|---|---|---|---|
| | of charcoal | 0 | 0.10% | 1.00% |
| Example 4-3 | Activated bamboo charcoal | — | 47.8 | 1.3 |
| Example 4-4 | Bincho charcoal | — | 32.5 | 3.3 |
| Example 4-5 | Activated Bincho charcoal | — | 2.8 | 3.3 |

In Table 16, all the charcoals adsorb bile acid (glycocholic acid). In particular, when charcoal was added by 1.00% in the activated bamboo charcoal administration group (Example 4-3), the Bincho charcoal administration group (Example 4-4), and activated Bincho charcoal administration group (Example 4-5), about 95% of bile acid was adsorbed and removed. Moreover, even when 0.10% charcoal was added in the activated Bincho charcoal administration group (Example 4-5), the adsorption and removal level was about the same as 1.00% charcoal addition. Accordingly, reabsorption of the bile acid can repress its circulation.

Example 5

The above Examples 1 to 4 confirmed the function of repressing the body weight gain by charcoal and health-promoting effects using mice or rats. Then, this Example 5 confirmed an effect of improving and repressing obesity of charcoal on humans using charcoal-mixed food developed. Specifically, using 24 subjects composed male and female adults with a BMI of 25 or more, the anti-obesity effect of charcoal-mixed food was discussed.

The trial design was conducted in compliance with placebo-controlled double-blind study. The trial food used was food containing no charcoal (hereinafter referred to as "control food") and food containing charcoal (hereinafter referred to as "subject food"). The 24 subjects selected after the pre-ingestion trial were allocated to 2 groups (Group I and Group II) by layer in consideration of age, gender, body weight, BMI, and percent body fat in the pre-check to allocate the control food and the subject food at random, and allowed to ingest trial food for 8 weeks. Regarding the dosage and administration of the trial food, the subjects were instructed to ingest one trial food, in principle, each in the morning, afternoon, and evening a day. If the subjects forget to ingest food in the morning and afternoon, they may ingest 3 trial foods in the evening, but they are not allowed to do so in the following days, and instructed to obey the rule as much as they can.

The control food (non-charcoal added) was in the form of stick jelly (20 g) obtained by properly combining sodium citrate: 50 mg, blackcurrant concentrated fruit juice: 200 mg, caramel coloring: 1500 mg, V. B1: 2 mg, and others: gelator/sweetener/acidulant/aroma chemical.

Meanwhile, trial food (charcoal-added) was in the form of stick jelly (20 g) obtained by properly combining sodium citrate: 50 mg, a charcoal-mixed powder (activated bamboo charcoal:activated Bincho charcoal=1:1): 3000 mg, blackcurrant concentrated fruit juice: 200 mg, V. B1: 2 mg, and others: gelator/sweetener/acidulant/aroma chemical.

The trial results will be described in detail as follows. The trial was conducted in a period from October 2016 to March 2017. With efficacy and safety of the subject food (charcoal-added) as evaluation items, a significance test was conducted by calculating the number of patients, mean value, and standard deviation for each item, and the statistical significance level was two-sided 5%. There were 24 subjects in this trial, 12 male and 12 female adults. In this trial, since one subject (trial food ingestion group) didn't complete the trial, the full analysis set (FAS) was 23 subjects. Also, since another subject who developed diabetes was removed from the analysis set, the per protocol set (PPS) was 22 subjects. The ingestion rate of trial food was 95% or more in all the 23 FAS subjects. In both FAS and PPS, there was no significant difference in ingestion rate among trial food groups.

<Evaluation of Efficacy>

(1) Main Evaluation Item (Body Weight, BMI, Percent Body Fat)

In this trial, the control food ingestion group increased the body weight, BMI, and percent body fat as a main evaluation item upon completion of ingestion by ingestion, and the subject food ingestion group decreased such values, but there was no significant difference among the trial food groups.

However, the control food ingestion group shows higher values, while the subject food ingestion group shows lower values, and P values by group comparison, as a variation by ingestion, are 0.230, 0.199, and 0.300 for body weight, BMI, and percent body fat, respectively, and in consideration thereof, it is believed that noticeable effects can be provided by longer ingestion periods and more subjects. Each of the items will be described as follows.

Body Weight:

A comparison of measured values over time found no statistically significant difference. Also, a comparison of measured values among trial food groups found no statistically significant difference. A comparison of variations by ingestion among trial food groups found no statistically significant difference.

BMI:

A comparison of measured values over time found no statistically significant difference. Also, a comparison of measured values among trial food groups found no statistically significant difference. A comparison of variations by ingestion among trial food groups found no statistically significant difference.

Percent Body Fat:

A comparison of measured values over time found no statistically significant difference. Also, a comparison of measured values among trial food groups found no statistically significant difference. A comparison of variations by ingestion among trial food groups found no statistically significant difference.

(2) Collateral Evaluation Item (Blood Lipid Level)

In blood lipids (T-Cho, LDL-Cho, HDL-Cho, TG) as a collateral evaluation item, there was no significant difference in variations by ingestion among trial food groups upon completion of ingestion. In this trial, 9 subjects (PPS) in T-Cho, 7 subjects (PPS) in LDL-Cho, and 4 subjects (PPS) in TG indicated the values above the reference value, and one subject in HDL-Cho indicated the value below the reference value, which accounts for a small proportion of all the subjects, and there were many subjects having normal values, thereby seemingly making it difficult to evaluate effects of subject food.

Comparison Over Time:

A comparison of measured blood lipid levels over time by ingestion found statistically significant variations for the following items.

T-Cho: In the subject food ingestion group, a comparison of the value of 209.5±37.2 mg/dL before the start of ingestion and the value of 223.4±35.7 mg/dL after the completion of ingestion found statistically significant increases ($p<0.05$).

LDL-Cho: In the subject food ingestion group, a comparison of the value of 131.9±36.3 mg/dL before the start of ingestion and the value of 140.4±35.3 mg/dL after the completion of ingestion found statistically significant increases ($p<0.05$).

Comparison Among Trial Food Groups:

A comparison of measured blood lipid levels among trial food groups found no statistically significant difference for all the items.

(3) Intestinal Flora

In intestinal flora as a collateral evaluation item, there was no significant difference in variations by ingestion among trial food groups upon completion of ingestion. Regarding the condition of defecation, a comparison of variations by ingestion in the analysis for PPS with the control food ingestion group upon completion of ingestion found a significantly large number of days of defecation in the subject food ingestion group. According to a stratified analysis for subjects having 5 or less days of defecation before the start of ingestion, there was no significant difference in variations by ingestion among the trial food groups for all the items.

Comparison Over Time:

A comparison with measured intestinal floras before the start of ingestion over time found statistically significant variations for the following items.

*Bacteroides*: In the control food ingestion group, a comparison of the value of 41.32±18.13% before the start of ingestion and the value of 47.52±16.04% after the completion of ingestion found statistically significant increases ($p<0.05$).

*Clostridium* subcluster XIVa: In the subject food ingestion group, a comparison of the value of 11.87±4.92% before the start of ingestion and the value of 15.96±4.30% after the completion of ingestion found statistically significant increases ($p<0.01$).

*Clostridium* cluster IX: In the subject food ingestion group, a comparison of the value of 7.16±7.09% before the start of ingestion and the value of 2.88±2.88% after the completion of ingestion found statistically significant decreases ($p<0.05$).

Comparison Among Trial Food Groups:

A comparison of measured intestinal floras among trial food groups found that the subject food ingestion group showed a significant lower value of 0.00±0.00% than the control food ingestion group (0.40±0.58%) after the completion of ingestion of *Clostridium* cluster XI. There was no statistically significant difference for other items. A comparison of variations by ingestion among trial food groups found no statistically significant difference for all the items.

(4) Condition of Defecation

At the time of (before the start of ingestion, one week after ingestion, two weeks after ingestion, 3 weeks after ingestion, 4 weeks after ingestion, 5 weeks after ingestion, 6 weeks after ingestion, 7 weeks after ingestion, after the completion of ingestion) in PPS (20 subjects), the number of defecation a week and days of defecation, properties of each defecation and odor, and variations by ingestion were measured. In addition, the results of the stratified analysis for (13) subjects having the number of defecation of 5 or less in the pre-observation period at each time were confirmed. Also, since the condition before the start of ingestion, regarding the condition of defecation, for each of the items was not so unfavorable, it seems difficult to evaluate the effects of subject food.

Comparison Over Time in PPS:

A comparison of the condition of defecation over time with that before the start of ingestion found statistically significant variations for the following items.

Number of defecation/week: In the control food ingestion group, a comparison of the value of 6.5±3.3 before the start of ingestion and the value of 13.7±7.2 3 weeks after ingestion found statistically significant increases (p<0.01). In the subject food ingestion group, a comparison of the value of 4.6±1.1 before the start of ingestion, the value of 10.1±5.4 3 weeks after ingestion, the value of 5.6±1.9 4 weeks after ingestion, the value of 5.7±1.7 6 weeks after ingestion, and the value of 6.3±1.8 after the completion of ingestion found statistically significant increases (4 weeks after ingestion: p<0.05, 3 weeks after ingestion, 6 weeks after ingestion, after the completion of ingestion: p<0.01).

Number of days of defecation/week: In the subject food ingestion group, a comparison of the value of 4.4±0.8 days before the start of ingestion, the value of 5.2±1.5 days 4 weeks after ingestion, the value of 5.2±1.4 days 5 weeks after ingestion, the value of 5.2±1.3 days 6 weeks after ingestion, and the value of 5.6±1.3 days after the completion of ingestion found statistically significant increases (4 weeks after ingestion, 5 weeks after ingestion: p<0.05, 6 weeks after ingestion, after the completion of ingestion: p<0.01).

Comparison Among Trial Food Groups in PPS:

A comparison of the condition of defecation among trial food groups with the value of 3.1±0.3 in the control food ingestion group 6 weeks after ingestion of the property found a significant low value of 2.6±0.6 in the subject food ingestion group. A comparison with the value of 3.1±0.3 in the control food ingestion group 6 weeks after ingestion of odor found a significant low value of 2.6±0.7 in the subject food ingestion group. There was no statistically significant difference for other items.

A comparison of variations by ingestion among trial food groups with the value of 0.4±1.1 days in the control food ingestion group after the completion of ingestion of the number of days of defecation/week found a significant high value of 1.3±0.9 days in the subject food ingestion group. There was no statistically significant difference for other items.

Comparison of subjects having the number of defecation before the start of ingestion of 5 or less over time:

A comparison of the condition of defecation over time with that before the start of ingestion found statistically significant variations for the following items.

Number of defecation/week: In the subject food ingestion group, a comparison of the value of 4.2±0.7 before the start of ingestion, the value of 9.9±5.9 3 weeks after ingestion, the value of 5.0±1.4 5 weeks after ingestion, the value of 5.2±1.3 6 weeks after ingestion, and the value of 5.8±1.4 after the completion of ingestion found statistically significant increases (3 weeks after ingestion, 5 weeks after ingestion: p<0.05, 6 weeks after ingestion, after the completion of ingestion: p<0.01).

Number of days of defecation/week: In the subject food ingestion group, a comparison of the value of 4.1±0.6 days before the start of ingestion, the value of 5.0±1.4 days 5 weeks after ingestion, the value of 4.9±1.2 days 6 weeks after ingestion, and the value of 5.3±1.2 days after the completion of ingestion found statistically significant increases (5 weeks after ingestion: p<0.05, 6 weeks after ingestion, after the completion of ingestion: p<0.01).

Comparison of subjects having the number of defecation before the start of ingestion of 5 or less among trial food groups:

A comparison of the condition of defecation among trial food groups with the value of 3.3±0.5 in the control food ingestion group 6 weeks after ingestion of the property found a significant low value of 2.6±0.6 in the subject food ingestion group. Also, a comparison of variations by ingestion among trial food groups found no statistically significant difference for all the items.

<Evaluation of Safety>

(1) Side Effect and Adverse Event

Regarding the safety of charcoal-containing food ingested at the 8th week, whether abnormal variations in anthropometry, physiological trials, and clinical tests are found and onset of adverse events were confirmed. In this trial, no side effect was confirmed.

Regarding adverse events, there were 6 cases for 5 subjects in the control food ingestion group, and 5 cases for 5 subjects in the subject food ingestion group. The incidence rate of adverse events was 41.7% (5/12) in the control food ingestion group, and 45.5% (5/11) in the subject food ingestion group. A comparison of whether adverse events are found among trial food groups found no statistically significant difference.

Adverse events in subjective symptom include "hemolytic streptococcal infection" and "human influenza type A" in the subject food ingestion group, and "cold symptom" in both of the trial food groups, both of which cases negated causality with trial food. Meanwhile, adverse events found in clinical tests are "diabetes area values (blood glucose, HbA1c, uric protein, urinary sugar)", "high TG value", "uric protein variations (+)" in the control food ingestion group, and high TG values in the subject food ingestion group, both of which cases negated causality with trial food. In addition, in this trial, no serious adverse events were confirmed. Therefore, it was judged that all adverse events in subjective symptoms in this trial have no causality with trial food based on periods of onset and circumstances.

Also, any variation in test values other than those described above is minor by a principal investigator, and is highly likely to be a physiological variation, and it was judged not to be clinically problematic. Consequently, since no serious variations or adverse events were confirmed, the safety was judged not to be problematic.

(2) Physiological Test (Blood Pressure, Pulse Rate)

A comparison of physiological tests by ingestion over time found no significant variation in all the trial food ingestion groups. Also, a comparison of measured values among trial food groups found statistically significant differences in diastolic blood pressure before the start of ingestion and pulse rate after the completion of ingestion, but these differences were judged not to be clinically significant. Both a comparison of other items over time and a comparison thereof among groups showed no statistically significant difference.

Comparison of Blood Pressure Over Time:

A comparison of measured values over time by ingestion found no statistically significant variation in all the trial food groups.

Comparison of Blood Pressure Among Trial Food Groups:

A comparison of measured values among trial food groups found statistically significant variations for the following items.

Diastolic blood pressure: A compared of the value of 83.5±7.7 mmHg after the start of ingestion in the control food group and the value of 76.2±7.3 mmHg before the start of ingestion in the subject food group found statistically significant differences (p<0.05).

A comparison of variations by ingestion among trial food groups found no statistically significant difference.

Variations in Blood Pressure of Individual Subjects:

The range of variations for individual subjects was −15 to 18 mmHg in systolic blood pressure, and −13 to 13 mmHg in diastolic blood pressure.

Comparison of Pulse Rate Over Time:

A comparison of measured values over time by ingestion found no statistically significant variation in all the trial food groups.

Comparison of Pulse Rate Among Trial Food Groups:

A comparison of measured values among trial food groups found statistically significant variations for the following items.

Pulse rate: A comparison of the value of 78.7±12.5 bpm after the completion of ingestion in the control food group and the value of 69.3±7.0 mEq/L after the completion of ingestion in the subject food group found statistically significant differences ($p<0.05$).

A comparison of variations by ingestion among trial food groups found no statistically significant difference.

Variations in Pulse Rate of Individual Subjects:

The range of variations for individual subjects was −15 to 22 bpm.

(3) Clinical Test (Biochemical Exam of Blood, Hematologic Test, Urine Qualitative Test)

In a biochemical exam of blood and a hematologic test as clinical tests in FAS (23 subjects), there were statistically significant increases in female CRE, Na, female RBC, and female Ht in the control food ingestion group after the completion of ingestion, and in Na in the subject food ingestion group, and statistically significant decreases in ALB and female CPK in the subject food ingestion group.

A comparison of measured values among trial food groups found statistically significant differences in BUN and PLT before the start of ingestion and BUN, female UA, WBC, and female Ht after the completion of ingestion, but these differences were judged not to be clinically significant. Also, a comparison of variations by ingestion among trial food groups found statistically significant differences in female CRE, but these differences were judged not to be clinically significant.

Comparison of Biochemical Exam of Blood Over Time:

A comparison of measured values with that before the start of ingestion over time found statistically significant variations for the following items.

ALB: In the subject food group, a comparison of the value of 4.35±0.24 g/dL before the start of ingestion and the value of 4.25±0.24 g/dL after the completion of ingestion found statistically significant decreases ($p<0.05$).

CPK (CK): In the female subject food group, a comparison of the value of 86.0±25.9 U/L before the start of ingestion and the value of 70.2±14.9 U/L after the completion of ingestion found statistically significant decreases ($p<0.05$).

CRE: In the female control food group, a comparison of the value of 0.703±0.124 mg/dL before the start of ingestion and the value of 0.763±0.150 mg/dL after the completion of ingestion found statistically significant increases ($p<0.05$).

Na: In the control food group, a comparison of the value of 140.9±1.8 mEq/L before the start of ingestion and the value of 142.2±1.3 mEq/L after the completion of ingestion found statistically significant increases ($p<0.05$).

In the subject food group, a comparison of the value of 140.3±1.8 mEq/L before the start of ingestion and the value of 141.9±1.6 mEq/L after the completion of ingestion found statistically significant increases ($p<0.01$).

Comparison of Biochemical Exam of Blood Among Trial Food Groups:

A comparison of measured values among trial food groups found statistically significant variations for the following items.

BUN (UN): A comparison of the value of 12.11±2.76 mg/dL before the start of ingestion in the control food group and the value of 9.68±2.76 mg/dL before the start of ingestion in the subject food group found statistically significant differences ($p<0.05$).

A comparison of the value of 13.35±2.62 mg/dL after the completion of ingestion in the control food group and the value of 10.18±2.17 mg/dL after the completion of ingestion in the subject food group found statistically significant differences ($p<0.01$).

UA: A comparison of the value of 5.55±1.19 mg/dL after the completion of ingestion in the female control food group and the value of 4.07±0.90 mg/dL after the completion of ingestion in the subject food group found statistically significant differences ($p<0.05$).

A comparison of variations by ingestion among trial food groups found statistically significant differences for the following items.

CRE: A comparison of the value of 0.600±0.041 mg/dL in the female control food ingestion group and the value of −0.013±0.023 mg/dL in the subject food ingestion group found statistically significant differences ($p<0.01$).

Variations in Biochemical Exam of Blood of Individual Subject:

Some of the items other than those recited as adverse events showed deviation from the reference ranges, but all within the physiological variations.

Comparison of Hematologic Test Over Time:

A comparison of measured values with that before the start of ingestion over time found statistically significant variations for the following items.

RBC: In the female control food group, a comparison of the value of 452.7±24.6×10$^4$/μL before the start of ingestion and the value of 478.5±33.3×10$^4$/μL after the completion of ingestion found statistically significant increases ($p<0.05$).

Ht: In the female control food group, a comparison of the value of 42.80±1.31% before the start of ingestion and the value of 45.00±2.37% after the completion of ingestion found statistically significant increases ($p<0.05$).

Comparison of Hematologic Test Among Trial Food Groups:

A comparison of measured values among trial food groups found statistically significant variations for the following items.

WBC: A comparison of the value of 6486.8∓1492.5/μL after the completion of ingestion in the control food group and the value of 5572.7±1005.1/μL after the completion of ingestion in the subject food group found statistically significant differences ($p<0.05$).

Ht: A comparison of the value of 45.00±2.37% after the completion of ingestion in the female control food group and the value of 41.68±1.91% after the completion of ingestion in the subject food group found statistically significant differences ($p<0.05$).

PLT: A comparison of the value of 31.38±3.73×10$^4$/μL before the start of ingestion in the control food group and the value of 26.45±4.62×10$^4$/μL before the start of ingestion in the subject food group found statistically significant differences ($p<0.05$).

A comparison of variations by ingestion among trial food groups found no statistically significant difference for all the items.

Variations in Hematologic Test of Individual Subjects:

Some of the items showed deviation from the reference ranges, but all within the physiological variations.

Urine Qualitative Test:

In a urine qualitative test, the urinary protein and the urinary sugar showed some variations, but a comparison of judgment values with that before the start of ingestion over time and a comparison among trial food groups found no statistically significant difference. Other items demonstrated no variations showing abnormality.

In this manner, a trial was conducted by 8-week ingestion using control food (non-charcoal added) and subject food (charcoal-added). Consequently, regarding anti-obesity effects by 8-week ingestion of charcoal-containing food, there was no significant difference among trial food groups after the completion of ingestion in terms of body weight, BMI, and percent body fat, but a comparison with that before the start of ingestion found increases in the control food ingestion group and decreases in the subject food ingestion group. Regarding the safety, no serious variations or events attributed to trial food were found for all the items after confirming whether abnormal variations are found in physiological tests and clinical tests and onset of adverse events, and the safety of charcoal-containing food by 8-week ingestion was confirmed. From these findings, we consider verifying the effects by lengthening ingestion periods or using more subjects to obtain more precise data.

As described above, the present invention provides a functional food that utilizes health-promoting effects of charcoal, is readily ingested, has no adverse side effect, and has an effect of improving and repressing obesity. The term substantially is defined as a possible practical deviation, from the recited value, within the limits identified by a typical error of a measurement at hand in related art or within an error acceptable for practical purposes in related art.

The invention claimed is:

1. A functional food configured to improve and repress obesity, the functional food comprising:
    a charcoal composition including a mixture of (i) at least one of a bamboo charcoal and an activated bamboo charcoal, and (ii) an activated Bincho charcoal, wherein
    each of the activated bamboo charcoal, when present, and the activated Bincho charcoal has a bulk density within a range from 0.3 g/ml to 0.6 g/ml, an average particle diameter of 10 μm or smaller, a BET specific surface area within a range from 1000 $m^2/g$ to 1200 $m^2/g$, and an iodine adsorption amount within a range from 1000 mg/g to 1300 mg/g.

2. The functional food according to claim 1, comprising one of a mixture of the bamboo charcoal with an activated Bincho charcoal and a mixture of the activated bamboo charcoal with the activated Bincho charcoal.

3. The functional food according to claim 1, wherein, when the mixture includes the activated bamboo charcoal and the activated Binsho charcoal, the charcoal composition has a weight ratio of the activated bamboo charcoal to the activated Bincho charcoal of 1:1.

4. A method comprising:
    improving and repressing obesity by consuming a functional food comprising a charcoal composition that includes a mixture of a bamboo charcoal with the activated Bincho charcoal or a mixture of an activated bamboo charcoal with an activated Bincho charcoal.

5. The method according to claim 4, wherein said improving and repressing obesity includes improving and repressing obesity contemporaneously with a process of losing body weight.

6. The method according to claim 4, comprising:
    decreasing a ratio of white adipocytes to a body weight as a result of said consuming.

7. The method according to claim 4, comprising: increasing of a high-density lipoprotein (HDL) cholesterol level as a result of said consuming.

8. The method according to claim 4, comprising: reducing an asparate aminotransferase liver function value and an alanine transaminase liver function value in the blood as a result of said consuming.

9. The method according to claim 4, comprising:
    reducing creatinine and urea nitrogen as renal function values in the blood as a result of said consuming.

10. The method according to claim 4, comprising:
    as a result of said consuming, maintaining a value of A/G (albumin/globulin) ratio in the blood as indicia of a nutritional status at the same level as that associated with consuming a normal meal.

11. The method according to claim 4, comprising:
    maintaining a composition of an intestinal flora substantially unchanged in comparison with that corresponding to consumption of a normal meal.

12. The method according to claim 4, comprising developing adsorption of indole as a component of stool odor as a result of said consuming.

13. The method according to claim 4, comprising: causing adsorption of bile acid as result of said consuming.

14. The method according to claim 4, wherein said repressing comprises consuming the charcoal composition comprising the mixture of an activated bamboo charcoal with an activated Bincho charcoal with a weight ratio of the activated bamboo charcoal to the activated Bincho charcoal of 1:1.

* * * * *